United States Patent [19]
Braster et al.

[11] Patent Number: 5,502,659
[45] Date of Patent: Mar. 26, 1996

[54] METHOD AND APPARATUS FOR CALIBRATING MOISTURE SENSORS

[75] Inventors: Olaf F. Braster, Greenwood; Klaus C. Maier; W. Patrick McCarthy, both of Indianapolis, all of Ind.

[73] Assignee: Endress+Hauser, Inc., Greenwood, Ind.

[21] Appl. No.: 254,323

[22] Filed: Jun. 6, 1994

[51] Int. Cl.$^6$ .................................... G01C 25/00
[52] U.S. Cl. ............. 364/571.01; 73/3; 73/1 G; 324/669
[58] Field of Search ............... 364/571.01, 557, 364/569, 558, 571.07; 73/25.04, 29.01, 335.04, 73, 1 R, 3, 1 G; 340/716; 324/669, 672, 676, 689

[56] References Cited

U.S. PATENT DOCUMENTS

| | | | |
|---|---|---|---|
| 3,477,279 | 11/1969 | Perlaky. | |
| 3,671,912 | 6/1972 | La Sota. | |
| 3,787,650 | 1/1974 | Lewis. | |
| 4,081,988 | 4/1978 | Change et al.. | |
| 4,098,284 | 7/1978 | Yamada. | |
| 4,305,724 | 12/1981 | Micko. | |
| 4,590,789 | 5/1986 | Kunze. | |
| 4,647,371 | 3/1987 | Schmitt et al.. | |
| 4,649,281 | 3/1987 | Schmitt et al.. | |
| 4,703,664 | 11/1987 | Kirkpatrick et al.. | |
| 4,821,557 | 4/1989 | Beeson, III | 73/3 |
| 4,953,386 | 9/1990 | Pearman et al. | 73/3 |
| 5,003,810 | 4/1991 | Jepson et al. | 73/3 |
| 5,069,072 | 12/1991 | Taylor et al.. | |
| 5,199,308 | 4/1993 | Lawhon et al.. | |
| 5,217,692 | 6/1993 | Rump et al.. | |
| 5,233,861 | 8/1993 | Gore et al. | 73/3 |

OTHER PUBLICATIONS

"Trace moisture, relative humidity, pressure, & oxygen measurement HygroTwin 2850", Technical Information TI 007M/03/ae, Endress+Hauser, Dec., 1992.

*Primary Examiner*—Emanuel T. Voeltz
*Assistant Examiner*—Thomas Peeso
*Attorney, Agent, or Firm*—Barnes & Thornburg

[57] ABSTRACT

An apparatus and method are provided for calibrating a measuring transmitter which provides an output signal proportional to a parameter of interest measured by a sensor in the measuring transmitter without removing the measuring transmitter from its normal operating position. The apparatus includes a housing, a calibration sensor element located in the housing for sensing said parameter of interest, and a tube for coupling the housing to the measuring transmitter, thereby exposing the calibration sensor to the same parameter of interest as the measuring sensor in the measuring transmitter. The apparatus also includes a communication link for coupling the measuring sensor to the calibration sensor, and a processor for processing data related to the parameter of interest detected by the calibrating sensor, for comparing the processed data related to the parameter of interest detected by the calibrating sensor to processed data related to the parameter of interest detected by the measuring sensor, and for calibrating the measuring sensor based on the comparison.

11 Claims, 9 Drawing Sheets

METHOD AND APPARATUS FOR CALIBRATING MOISTURE SENSORS

BACKGROUND AND SUMMARY OF THE INVENTION

The present invention relates to a method and apparatus for calibrating a moisture sensor and transmitter. More particularly, the present invention relates to an improved calibration apparatus and method which permits automatic recalibration of a moisture transmitter in the field without disconnecting the moisture transmitter from a process pipe in which the moisture transmitter is installed.

Moisture measuring systems are well known for sensing moisture in a process pipe. Typical systems include remote transmitters with microprocessor electronics, a sensor element mounted in a probe, a flow chamber, a weather-proof enclosure and assorted fittings. The moisture probe can be installed on to a process pipe in a variety of ways. For instance, the moisture sensor can be mounted in an in-line mounting in a pipe, mounted in a pipe expansion, mounted in an elbow for small pipe diameters, or mounted in a by-pass line to facilitate removal of the moisture probe.

One problem associated with moisture transmitters is that the sensors need to be recalibrated, at least every year. Conventional moisture probes must be detached from the process pipe and sent back to the manufacturer for recalibration. For instance, in a common installation, a moisture probe is mounted in a bypass flow cell with a valve at the outlet. The transmitter provides a display and a current output. When recalibration is needed, the moisture probe must be removed from the process pipe and sent back to the factory for recalibration. This causes a down time of at least 2–3 weeks. After return of the moisture probe, new calibration data must be entered into the transmitter by changing an EPROM or programming through manual entry keys.

Advantageously, the apparatus and method of the present invention are designed to permit field calibration of the moisture transmitter without removing the moisture transmitter from the process pipe. Using the field calibrator, the moisture transmitter can be recalibrated in about 24 hours without removing the moisture transmitter from the process pipe. The recalibration is done on-site and automatically. The user does not have to be knowledgeable on how to use a moisture analyzer or maintain it. Conventional recalibration methods impose on the user a duty to know how to match the recalibrated sensor to the transmitter by entering data or opening the transmitter for an EPROM change.

According to one aspect of the present invention, an apparatus is provided for calibrating a measuring transmitter which provides an output signal proportional to a parameter of interest measured by a sensor in the measuring transmitter without removing the measuring transmitter from its normal operating position. The apparatus includes a housing, a calibration sensor element located in the housing for sensing said parameter of interest, and a tube for coupling the housing to the measuring transmitter, thereby exposing the calibration sensor to the same parameter of interest as the measuring sensor in the measuring transmitter. The apparatus also includes a communication link for coupling the measuring sensor to the calibration sensor, and means for processing data related to the parameter of interest detected by the calibrating sensor, for comparing the processed data related to the parameter of interest detected by the calibrating sensor to processed data related to the parameter of interest detected by the measuring sensor, and for calibrating the measuring sensor based on the comparison.

In the illustrated embodiment, the apparatus further includes means for storing original calibration data related to the parameter of interest from the measuring transmitter, a maximum detected value of the parameter of interest from both the measuring sensor and the calibration sensor, and a minimum detected value of the parameter of interest for both the measuring sensor and the calibration sensor. The apparatus also includes a signal generator for generating a period having a variable length as a function of the parameter of interest being measured.

Also in the illustrated embodiment, the apparatus includes a clock for generating equally spaced pulses, and means for determining a count of pulses occurring within a period representing the maximum detected value of the parameter of interest for the calibration sensor, a period representing the maximum detected value of the parameter of interest from the measuring sensor, a period representing the minimum detected value of the parameter of interest for the calibration sensor, and a period representing the minimum detected value of the parameter of interest for the measuring sensor.

The processing means further calculates a difference between the original calibration data for the maximum detected value of the parameter of interest and the maximum detected value of the parameter of interest from the calibration sensor and a difference between the original calibration data for the minimum detected value of the parameter of interest and the minimum detected value of the parameter of interest from the calibration sensor. A display unit is coupled to the processing means to provide a visual indication of the progress of the calibrating means.

According to another aspect of the present invention, a method is provided for recalibrating a measuring transmitter which provides an output signal proportional to a parameter of interest measured by a measuring sensor in the measuring transmitter without removing the measuring transmitter from its normal operating position. The method includes the steps of providing a calibration sensor for sensing said parameter of interest, and connecting the calibration sensor to the measuring transmitter device, thereby exposing the calibration sensor to the same parameter of interest as the measuring sensor. The method also includes the steps of processing data related to the parameter of interest detected by the calibrating sensor, comparing the processed data related to the parameter of interest detected by the calibrating sensor to processed data related to the parameter of interest detected by the measuring sensor, and recalibrating the measuring sensor based on the comparison.

Additional objects, features, and advantages of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
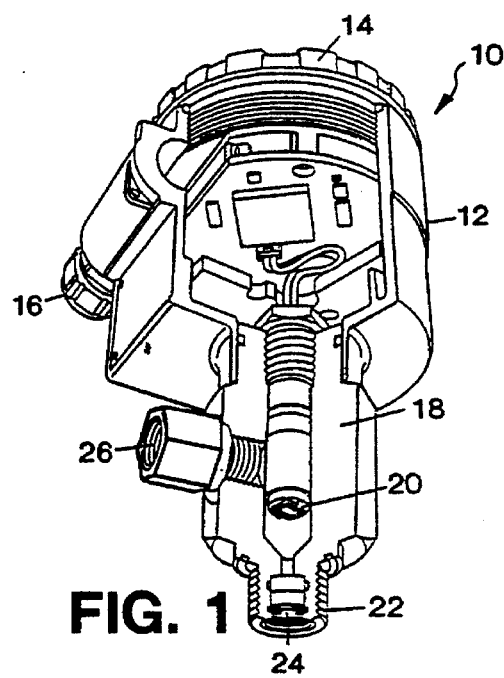
FIG. 1 is a perspective view with portions broken away illustrating details of a moisture transmitter for generating an output signal proportional to the moisture detected by a moisture sensor.

Referring now to the drawings, FIG. 1 illustrates a moisture transmitter 10 having an outer housing 12, a threaded cap portion 14, and a power signal cable entry 16. Illustratively, moisture transmitter is a DewPro MMY30 trace moisture transmitter available from Endress + Hauser located in Greenwood, Ind. Moisture transmitter 10 includes a flow cell 18 coupled to housing 12. A sensor element 20 is mounted within flow cell 18. Moisture transmitter 10 also includes a threaded inlet or process connection 22 having a sintered filter 24 mounted therein. Moisture transmitter 10 also includes an outlet or exhaust fitting 26 threadably coupled to flow cell 18. During normal operation, a plug having an orifice therein to bleed off process air is machined into the outlet fitting 26. Illustratively, moisture transmitter 10 provides a two-wire output signal represented by a 4–20 mA loop current which is directly proportional to the dew point temperature in °C. or °F. In the standard range, 4 mA corresponds to –90° C. (–130° F.) and 20 mA corresponds to +10° C. (+50° F.) dew point temperature.

Preferably, sensor element 20 is an aluminum oxide trace moisture sensor element operating under the capacitance principle. Sensor element 20 is available from Endress + Hauser in Greenwood, Indiana. Sensor element 20 provides longer calibration stability, excellent corrosion resistance, and improved speed of response. Sensor element 20 is mounted on a ceramic substrate and has a reduced temperature coefficient.

Figure 2:
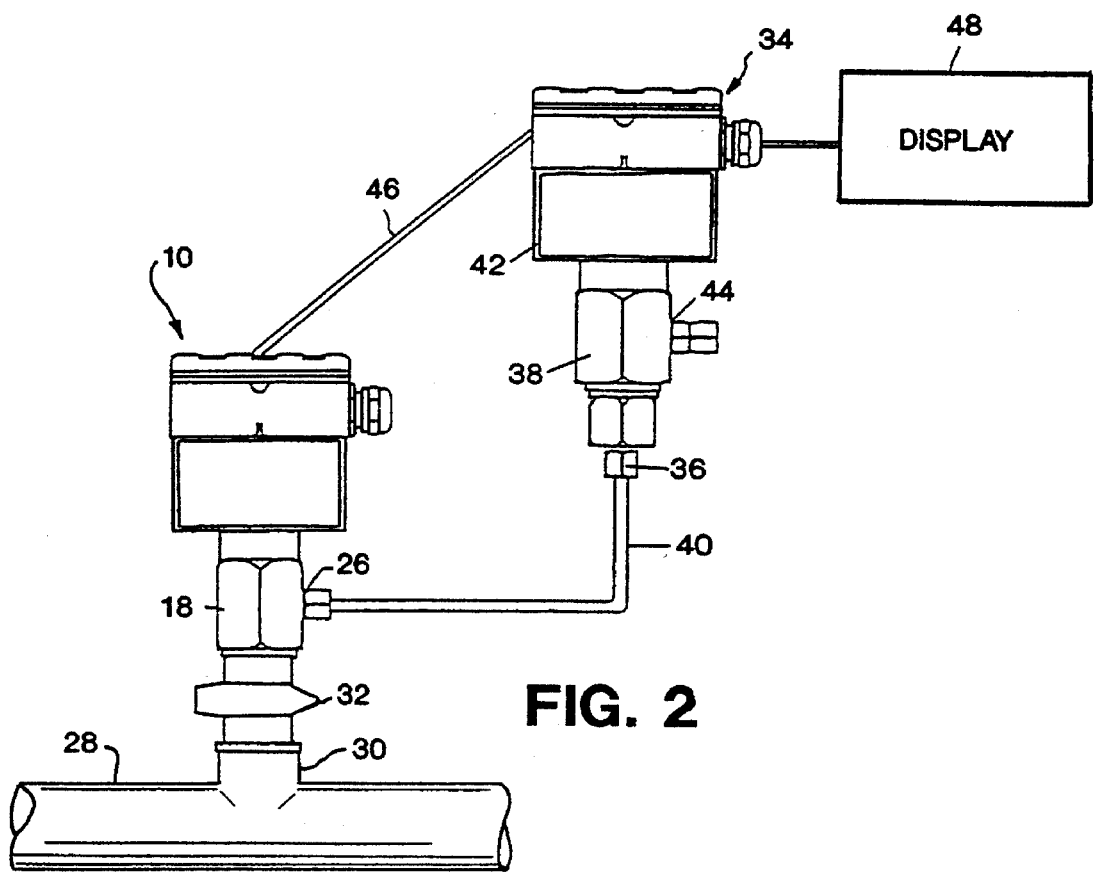
FIG. 2 is a diagrammatical view illustrating the moisture transmitter of FIG. 1 coupled to a process pipe and a calibrator coupled to the moisture transmitter for calibrating the moisture transmitter in the field without removing the moisture transmitter from the process pipe.

Typically, moisture transmitter 10 is calibrated at the factory to precise National Institute of Standards and Technology (NIST) certified moisture references and has an accuracy of within ±2° C. dew point. FIG. 2 illustrates moisture transmitter 10 mounted within a process pipe 28. Illustratively, moisture transmitter 10 is mounted within a process fitting 30. A shut-off valve 32 is coupled to flow cell 18 of moisture transmitter 10. When recalibration of moisture transmitter 10 is required, a calibrator unit 34 is coupled to moisture transmitter 10 as illustrated in FIG. 2. Specifically, an inlet connection 36 of calibrator 34 is coupled to flow cell 38 of calibration sensor 34. A tube 40 is coupled between outlet fitting 26 of moisture transmitter 10 and inlet connection 36 of calibrator 34. Illustratively, tube 40 is a ¼ inch (6 mm) tube. Calibrator 34 is coupled in series with moisture transmitter so that calibrator 34 is exposed to the same process air under pressure as moisture transmitter 10. Fitting 44 includes an orifice which bleeds off process air.

Calibrator 34 is structurally identical to moisture sensor 10 discussed above. Calibrator 34 includes an electronic housing 42, an outlet fitting 44, an aluminum oxide sensor, and a transmitter. Calibrator 34 is electronically coupled to moisture transmitter 10 by a RS 485 communication link 46. Calibration sensor 34 is also electrically coupled to a display unit 48 which provides a visual indication of the progress of the calibrator 34 when recalibrating moisture transmitter 10.

Figure 3:
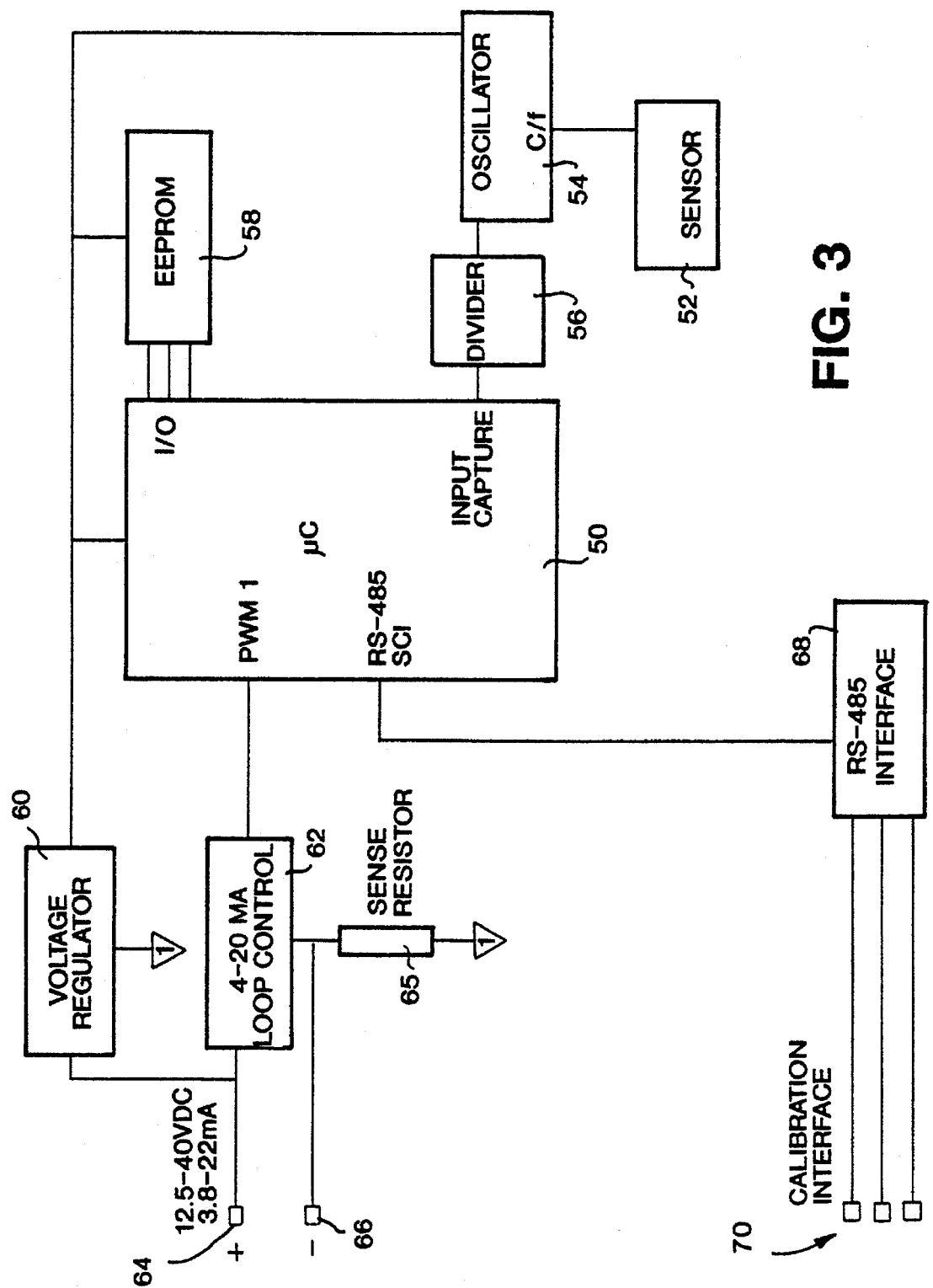
FIG. 3 is a block diagram illustrating the electronic circuitry of the calibrator.

FIG. 3 is a block diagram of the electronics of the calibrator 34. A microcontroller 50 is provided for controlling the electronics to process information from the calibrator 34 and to recalibrate moisture transmitter 10 as discussed below in detail. A sensor 52 is provided for detecting the parameter of interest. Illustratively, sensor 52 is an aluminum oxide trace moisture sensor operating under the capacitance principle. Sensor 52 is coupled to an oscillator 54. Oscillator 54 is coupled to a divider circuit 56. An output of divider circuit 56 is coupled to an input capture pin of microcontroller 50.

Calibration data is stored in an EEPROM 58. EEPROM 58 is electrically coupled to I/O pins of microcontroller 50. A voltage regulator 60 is provided to supply power to the various electronic components of the calibrator 34. A loop control circuit 62 is provided to generate an output signal ranging from 4–20 mA indicative of the parameters of interest measured by sensor 52. Illustratively, the output from loop control 62 across terminals 64 and 66 is a dew point temperature in °C. or °F. A sense resistor 65 is provided. Sense resistor measures total current draw of the calibrator and adjusts a voltage to current converter in loop control circuit 62 to maintain the output signal between 4–20 mA proportional to the dew point.

A RS-485 communication interface 68 is coupled to microcontroller 50. Interface 68 is configured to be coupled to moisture transmitter 10 by calibration interface 70 to permit calibrator 34 to recalibrate moisture transmitter 10.

Figure 4A:
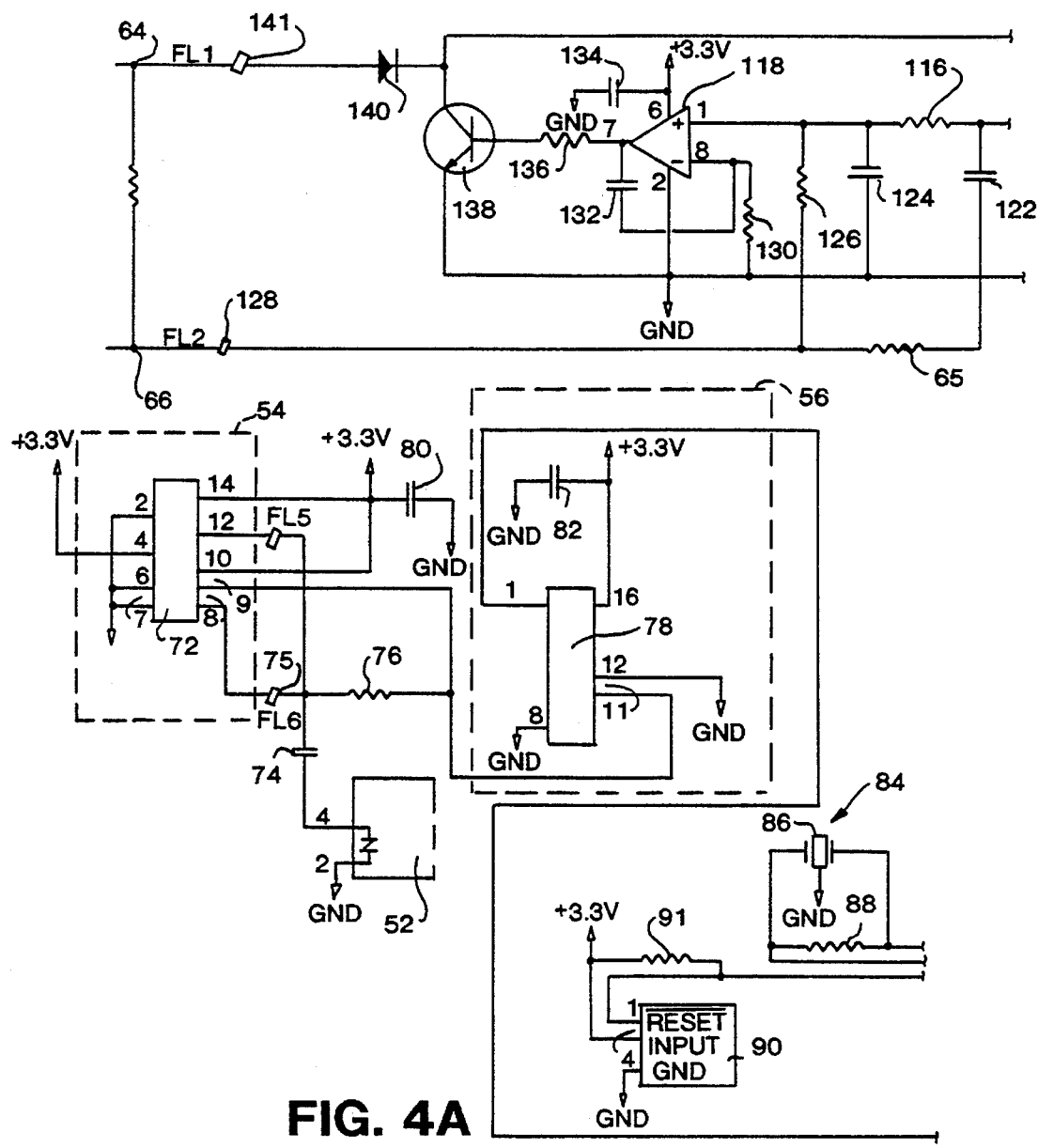
FIG. 4A and 4B are schematic diagrams of the calibration sensor control circuitry.
Figure 4B:
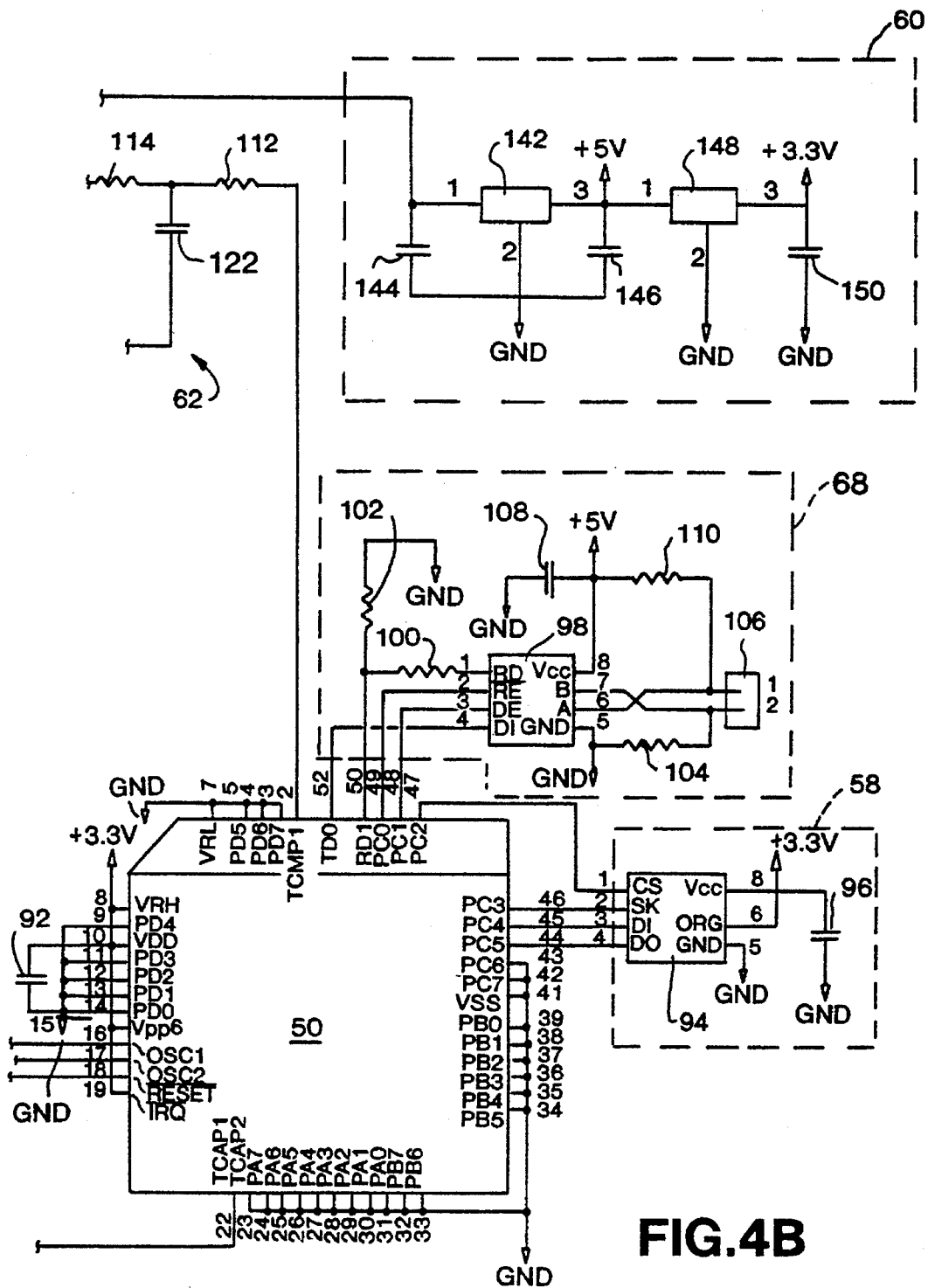

Details of the electronic circuitry of calibrator 34 are illustrated in FIGS. 4A and 4B. Microcontroller 50 is illustratively a model number MC68HC705B5 available from Motorola. Oscillator 54 is illustratively a model number ICL7556 oscillator integrated circuit chip 72 available from Maxim. Pins 2, 6 and 7 of chip 72 are coupled to ground. Pin 4 of chip 72 is coupled to a +3.3 V supply voltage. Pin 8 of chip 72 is coupled through a 33 nF capacitor 74 to pin 4 of moisture sensor 52. Pin 2 of moisture sensor 52 is coupled to ground. Pin 8 of chip 72 is coupled to pin 9 of chip 72 through a ferrite bead 75 and a 10K resistor 76. Ferrite bead 75 is a model number 2643021801 from Fair-Rite. Pin 9 of chip 72 is also coupled to pin 11 of a divider integrated circuit chip 78. Chip 78 is a model 74HC4060D available from Signetics. Pin 10 of chip 72 is coupled to the +3.3 V supply voltage. Pin 12 of chip 72 is coupled to the common terminal of ferrite bead 75 and resistor 76. Pin 10 of chip 72 is also coupled through a 100 nF capacitor 80 to ground. Pin 14 of chip 72 is coupled to the +3.3 V supply voltage. In addition, pin 14 is coupled through capacitor 80 to ground.

Pin 1 of divider chip 78 is coupled to a first input capture pin 22 of microcontroller 50. Pins 8 and 12 of chip 78 are coupled to ground. Pin 16 of chip 78 is coupled to the +3.3 V supply voltage. In addition, pin 16 of chip 78 is coupled through a 100 nF capacitor 82 to ground.

A 2 MHz clock 84 includes a 2 MHz oscillator 86 coupled in parallel with a 1M resistor 88 between pins 16 and 17 (OSC1 and OSC2) of microcontroller 50. Pin 1 of low voltage interrupt chip 90 is coupled to pin 18 of microcontroller 50. Pin 1 of chip 90 is also coupled through a 10K resistor 91 to pin 2 of chip 90. Pin 2 of chip 90 is coupled to the +3.3 V supply voltage. Pin 4 of chip 90 is coupled to ground. Chip 90 measures the supply voltage and resets the microcontroller 50 if the voltage drops below a preset value.

Pins 4, 5, 7, 9, 11–14, 23–39, and 41–43 of microcontroller 50 are all coupled to ground. Pins 8, 10, 15, and 19 of microcontroller 50 are coupled to the +3.3 V supply voltage. Pin 10 of microcontroller 50 is coupled through a 100 nF capacitor 92 to ground.

Pin 44 of microcontroller 50 is coupled to pin 4 of EEPROM chip 94. Illustratively, chip 94 is a AT93C66-10SI EEPROM chip available from Atmel. Pin 44 of microcontroller 50 is coupled to pin 4 of chip 94. Pin 45 of microcontroller 50 is coupled to pin 3 of chip 94. Pin 46 of microcontroller 50 is coupled to pin 2 of chip 94. Pin 47 of microcontroller 50 is coupled to pin 1 of chip 94.

Pin 5 of chip 94 is coupled to ground. Pin 6 of chip 94 is coupled to pin 8 of chip 94. The common terminal of pin 6 and pin 8 is coupled to the +3.3 V supply voltage. In addition, the common terminal of pins 6 and 8 are coupled through a 100 nF capacitor 96 to ground.

Pin 48 of microcontroller 50 is coupled to pin 3 of communication interface chip 98. Illustratively, chip 98 is a LTC485 chip available from Linear Tech. Pin 49 of microcontroller 50 is coupled to pin 2 of chip 98. Pin 50 of microcontroller 50 is coupled through a 56K resistor 100 to pin 1 of chip 98. In addition, pin 50 of chip 50 is coupled through a 93.1K resistor 102 to ground. Pin 52 of microcontroller 50 is coupled to pin 4 of chip 98. Pin 5 of chip 98 is coupled to ground. Pin 5 of chip 98 is also coupled through a 1M resistor 104 to pin 2 of connector 106. Pin 6 of chip 98 is coupled to pin 1 of connector 106. Pin 7 of chip 98 is coupled to pin 2 of connector 106. Pin 8 of chip 98 is coupled to a +5 V supply voltage. Pin 8 is also coupled through a 100 nF capacitor 108 to ground. In addition, pin 8 of chip 98 is coupled through a 1M resistor 110 to pin 1 of connector 106.

Pin 2 of microcontroller 50 is coupled to loop control circuit 62. Specifically, pin 2 of microcontroller 50 is coupled through a 1M resistor 112, a 1M resistor 114, and a 1M resistor 116 to the + input terminal of operational amplifier 118. Operational amplifier is a model number LT1078IS8 available from Linear Tech. The common terminal of resistors 112 and 114 is coupled to ground through a 100 nF capacitor 120. A common terminal of resistors 114 and 116 is coupled to ground through a 1 nF capacitor 122. The + input terminal at pin 1 of operational amplifier 118 is coupled through a 1 nF capacitor 124 to ground. Pin 1 of operational amplifier 118 is also coupled through a 221K resistor 126 and a 10 ohm sense resistor 65 to ground. A common terminal of resistors 126 and 65 is coupled through a ferrite bead 128 to output terminal 66. The − input terminal of operational amplifier 118 at pin 8 is coupled through a 205K resistor 130 to ground. Pin 8 of operational amplifier 118 is also coupled through a 22 nF capacitor 132 to the output terminal of operation amplifier 118 at pin 7. Pin 2 of operational amplifier 118 is coupled to ground. Pin 6 of operational amplifier 118 is coupled to the +3.3 V supply voltage. In addition, pin 6 of operational amplifier 118 is coupled through a 100 nF capacitor 134 to ground. The output terminal at pin 7 of operational amplifier 118 is coupled through a 10K resistor 136 to the base of transistor 138. Illustratively transistor 138 is a MJD31 transistor available from Motorola. The emitter of transistor 138 is coupled to ground. The collector of transistor 138 is coupled to the cathode of diode 140. Diode 140 is illustratively a LL4148 diode available from ITT. The anode of diode 140 is coupled through ferrite bead 141 to terminal 64. The collector of transistor 138 is also coupled to terminal 1 of voltage regulator 142. Illustratively, voltage regulator 142 is a LT1121-IST-5.0 regulator available from Linear Tech. Pin 1 of regulator 142 is coupled through a 100 nF capacitor 144 to ground. Pin 2 of regulator 142 is coupled to ground. Pin 3 of regulator 142 is coupled to a +5 V supply voltage. Pin 3 of regulator 142 is also coupled through a 1 uF capacitor 146 to ground. In addition, pin 3 of regulator 142 is coupled to pin 1 of voltage regulator 148. Illustratively, voltage regulator 148 is a LT1121-IST-3.3 regulator available from Linear Tech. Pin 2 of regulator 148 is coupled to ground. Pin 3 of regulator 148 is coupled to the +3.3 V supply voltage. Pin 3 of regulator 148 is also coupled through a 1 uF capacitor 150 to ground.

Figure 5:
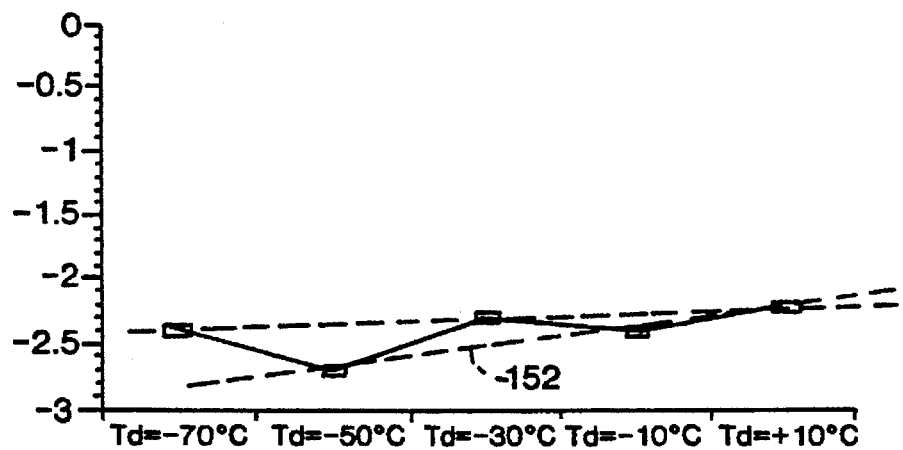
FIGS. 5–7 are graphs illustrating dew point temperature drift of a moisture transmitter over time.
Figure 6:
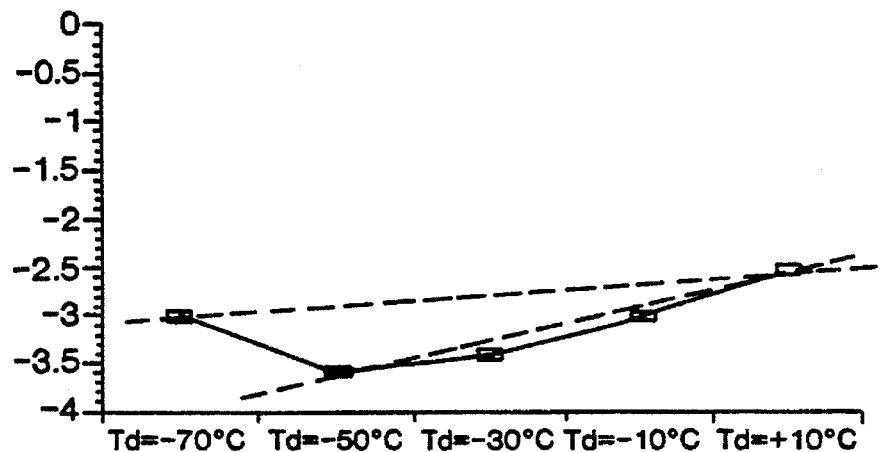
Figure 7:
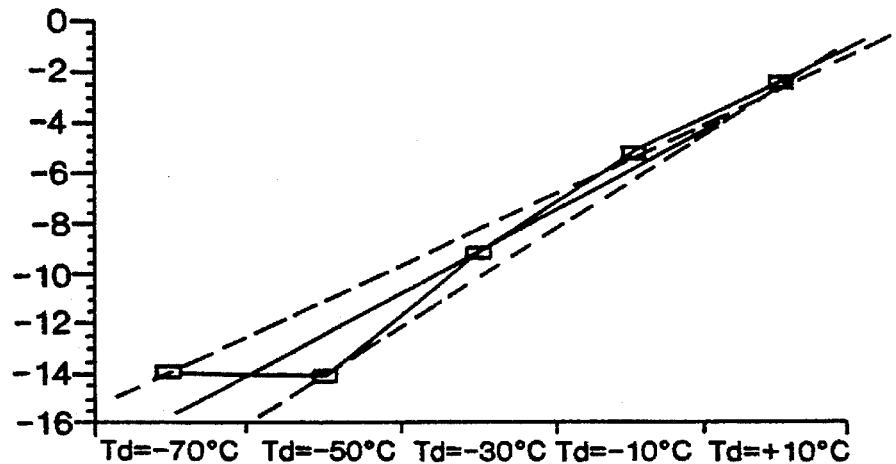

FIG. 5 is a table illustrating dew point temperature drift of a moisture transmitter which has been operated for 7 months at normal room temperature of 15° C. to 30° C. and dry air. The slope of a line through the maximum and minimum points is illustrated by dotted line 152. FIG. 6 illustrates a table for a moisture transmitter which has been continuously in dry air with a dew point of −90° C. for nine months. FIG. 7 is a table illustrating a worst case application in dry air at an elevated temperature of 60° C. A freshly calibrated sensor would have a straight line running across the zero degree dew point temperature drift line in all three FIGS. 5, 6, and 7. As illustrated in FIG. 7, the moisture transmitter had substantial dew point temperature drift after being exposed to the elevated temperature. After such a drift acceptable limits are exceeded and it is necessary to recalibrate the moisture transmitter.

Figure 8:
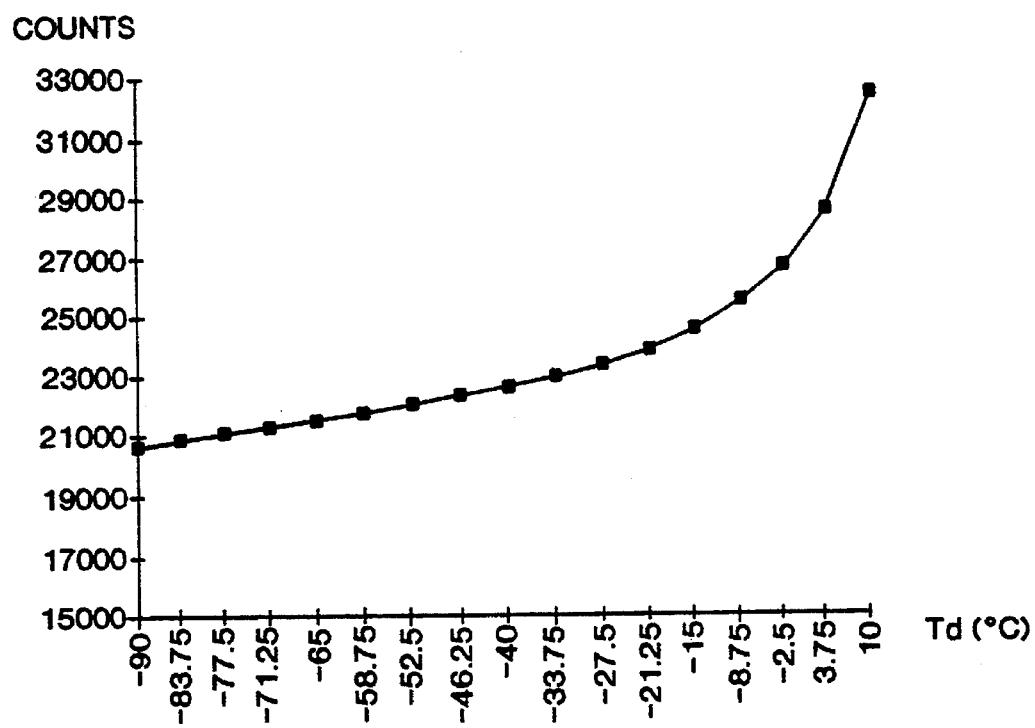
FIG. 8 is a graph illustrating the number of counts corresponding to various dew point temperatures which are programmed into a moisture transmitter to permit conversion of a capacitance sensor signal into an output signal proportional to the dew point temperature.

At the factory, moisture transmitter 10 is loaded with data corresponding to a temperature range of −90° C. to +10° C. corresponding to the 4–20 mA loop current. The oscillator associated with the moisture sensor 20 produces signals having different periods as a function of the capacitance of the sensor 20. A clock produces signals which are counted during each period to produce a number of counts for each period. The number of counts generated within each period associated with the moisture sensor 20 are determined and loaded into the memory of moisture transmitter 10. A sample of such data is as follows and is illustrated graphically in FIG. 8:

| Dew point Temperature (°C.) | Counts |
| --- | --- |
| −90.00 | 20692 |
| −83.75 | 20910 |
| −77.50 | 21110 |
| −71.25 | 21320 |
| −65.00 | 21529 |
| −58.75 | 21792 |
| −52.50 | 22079 |
| −46.25 | 22362 |
| −40.00 | 22646 |
| −33.75 | 22999 |
| −27.50 | 23403 |
| −21.25 | 23890 |
| −15.00 | 24573 |

-continued

| Dew point Temperature (°C.) | Counts |
|---|---|
| −8.75 | 25509 |
| −2.50 | 26673 |
| 3.75 | 28561 |
| 10.00 | 32447 |

During normal operation, sensor 20 of moisture transmitter 10 changes capacitance as dew point temperature changes, thereby creating signals having periods of various lengths. The period affects the number of counts detected by a microprocessor within each period within moisture transmitter 10. The counts detected are correlated back to the table discussed above. From that table, the microprocessor of moisture transmitter 10 generates an output current proportional to the calculated dew point temperature.

Figure 9:
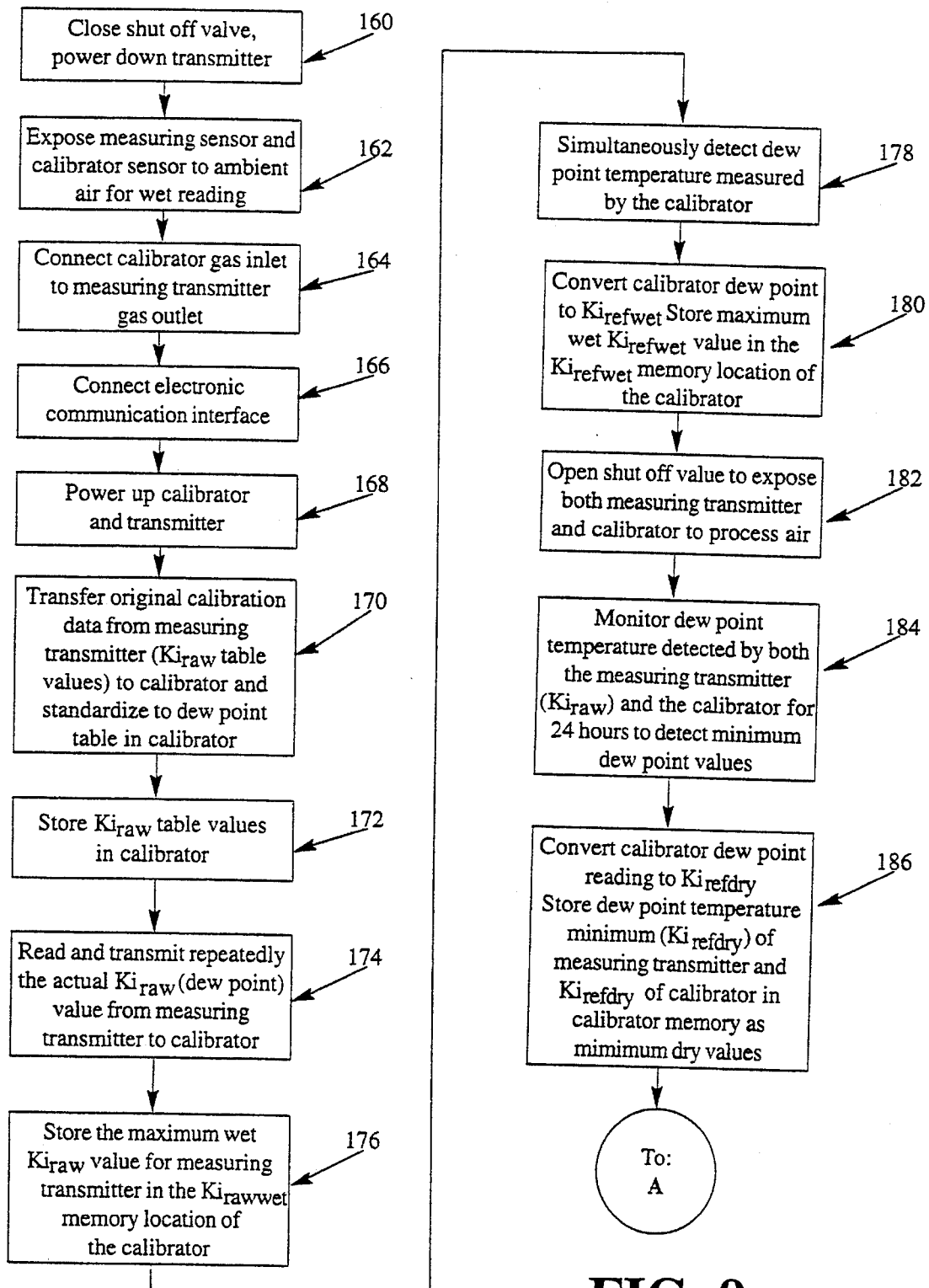
FIG. 9 is a flow chart illustrating the steps performed by the calibrator to recalibrate the moisture transmitter while the moisture transmitter is still connected to the process pipe.
Figure 10:
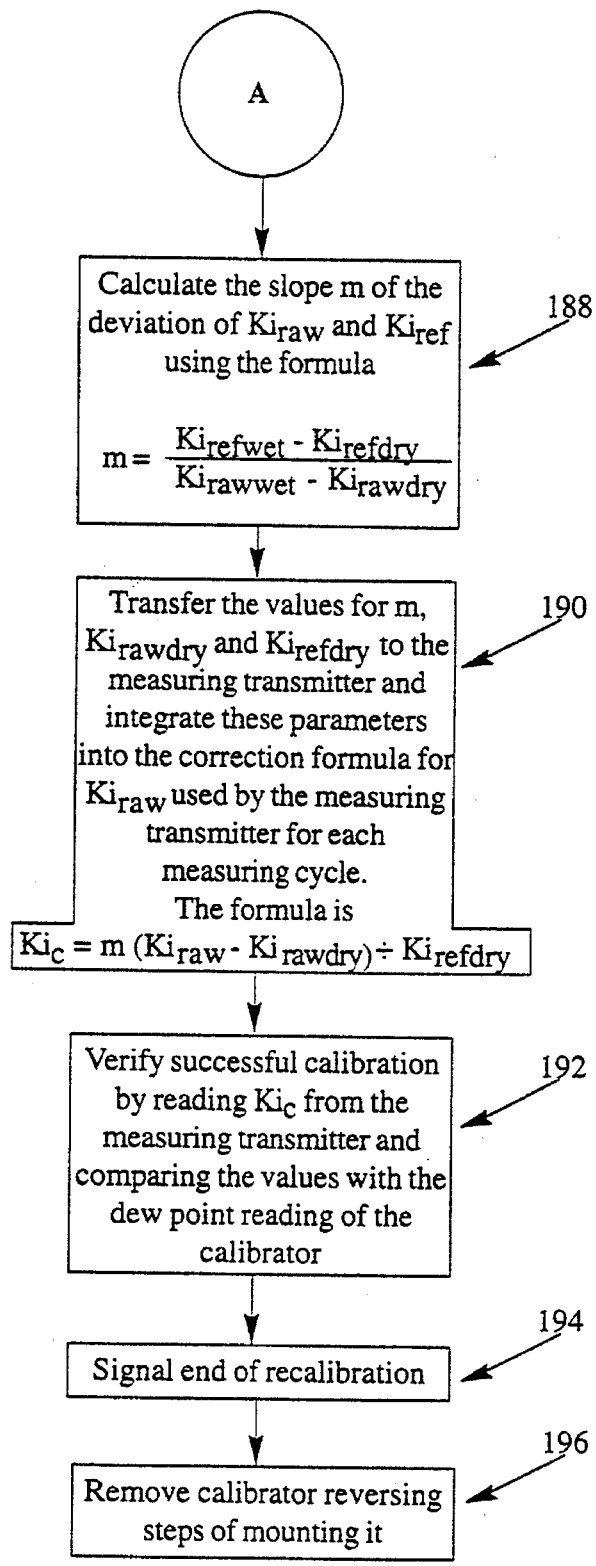
FIG. 10 is a flow chart illustrating further steps performed by the calibrator to recalibrate the moisture transmitter.

After a certain period of time, however, moisture transmitter 10 needs to be recalibrated. At that time, calibrator 34 is coupled to moisture transmitter 10 as discussed above. FIGS. 9 and 10 illustrate a flow chart of the steps performed by the software and hardware components of calibrator 34 to recalibrate moisture transmitter 10. First, shut-off valve 32 is closed to block process air from flowing into moisture transmitter 10 and the transmitter is powered down. This step is illustrated at block 160 of FIG. 9. Next, a plug 26 is removed and line 40 is attached to couple calibrator 34 in series with moisture transmitter 10. Before calibrator 34 and moisture transmitter 10 are coupled together, sensor 20 of moisture transmitter 10 and sensor 52 of calibrator 34 both need to be exposed to ambient air for 5 minutes as illustrated at block 162. Ambient air is typically referred to as "wet" air having a dew point temperature of between 0°–10° C. After calibrator 34 is coupled to moisture transmitter 10 as illustrated at block 164, the calibration interface 70 is coupled to moisture transmitter 10 to provide a digital serial communication link 46 between calibrator 34 and moisture transmitter 10. This step is illustrated in block 166.

Next, power is turned on to calibrator 34 and measuring transmitter 10 as illustrated at block 168. The original table of calibration data stored in moisture transmitter 10 is then transferred to calibrator 34 over communication link 46 as illustrated at block 170. This original calibration data is stored in EEPROM 58 of calibrator 34 as illustrated at block 172.

Next, the dew point temperature measured by moisture transmitter 10 is detected at block 174. This detected dew point temperature is a maximum dew point temperature for the wet air reading. Typically, the maximum will occur within five minutes of removing plug 26 of the transmitter 10 due to the exposure of the sensors to ambient air. The maximum wet value for the moisture transmitter 10 is stored in EEPROM 58 of calibrator 34 as illustrated at block 176. The dew point temperature measured by calibrator 34 is also detected as illustrated at block 178. The maximum wet value for the dew point temperature measured by calibrator 34 is converted to reference counts $Ki_{refwet}$ and stored in EEPROM 58 of calibrator 34 as indicated at block 180. The shut-off valve 32 is then open to expose both moisture transmitter 10 and calibrator 34 to process air from process pipe 28. Process air is supplied under pressure to both measuring transmitter 10 and calibrator 34. As discussed above, calibrator 34 is coupled in series with moisture transmitter 10 so that sensors 20 and 52 are exposed to the same process air almost simultaneously. This step is illustrated at block 182.

The dew point temperatures detected by both the moisture transmitter 10 and calibrator 34 are monitored for about 24 hours in order to detect minimum dew point values as illustrated at block 184. The minimum dew point temperatures detected by both moisture transmitter 10 and calibrator 34 are stored in EEPROM 58 of calibrator 34 as minimum "dry" values for the dew point temperature as illustrated in block 186. After the minimum dew point temperature values for both the moisture transmitter 10 and the calibrator 34 are stored, calibrator 34 begins its recalibration procedure of moisture transmitter 10. $Ki_{rawwet}$ is the number of counts corresponding to the maximum wet dew point temperature detected by moisture transmitter 10. The variable $Ki_{rawdry}$ is the number of counts corresponding to the minimum dew point temperature detected by moisture transmitter 10. Calibrator 34 has calculated the number of counts using original data from moisture transducer to achieve the accurate dew point maximum temperature and dew point minimum temperatures measured by calibrator 34. Since calibrator 34 has been recently calibrated at the factory, it is assumed that the maximum and minimum values detected by the calibrator are the actual maximum and minimum values of the dew point temperature. $Ki_{refwet}$ is a variable representing the number of counts in the original stored moisture transmitter calibration data required to generate the maximum dew point temperature detected by calibrator 34. The variable $Ki_{refdry}$ represents the number of counts from the original stored moisture transmitter 10 required to generate the minimum dew point temperature measured by calibrator 34. This step is illustrated at blocks 180 and 186.

Figure 11:
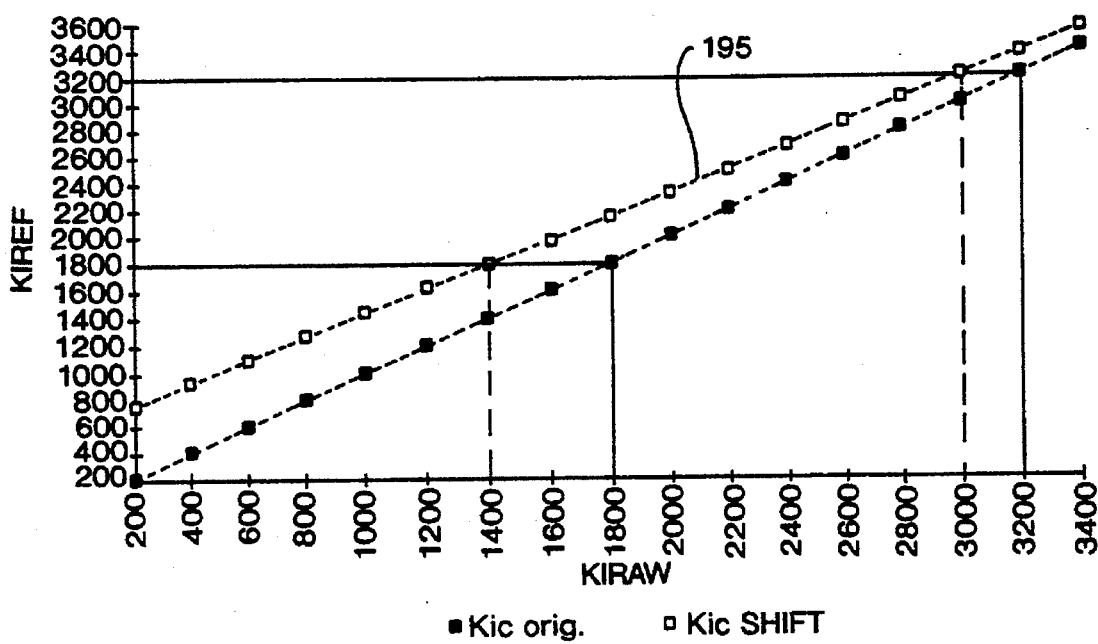
FIG. 11 is a graph illustrating the counts corresponding to dew point temperatures measured by a moisture transmitter versus the counts corresponding to dew point temperatures measured by the calibrator.

A graphic illustration of the detected data is illustrated in FIG. 11. After first factory calibration, $Ki_{raw}$ counts equal the $Ki_{ref}$ counts (e.g. see $Ki_{raw}$ at 3200 and 1800 counts). The slope of the lower line in FIG. 11 corresponding to the original factory setting is 1, the offset is zero. After a drift, $Ki_{rawwet}$ (e.g. 3200) and $Ki_{rawwet}$ (e.g. 1400) counts read lower, referencing the new counts of $Ki_{raw}$ to the required $Ki_{ref}$ wet and dry values (3200 and 1800). Line 195 represents the new relation between $Ki_{raw}$ and $Ki_{ref}$. Calibrator 34 next calculates the slope of line 195 in FIG. 11 using the following equation:

$$m = \frac{Ki_{refwet} - Ki_{refdry}}{Ki_{rawwet} - Ki_{rawdry}}$$

This step is illustrated as step 188 in FIG. 10.

Figure 12:
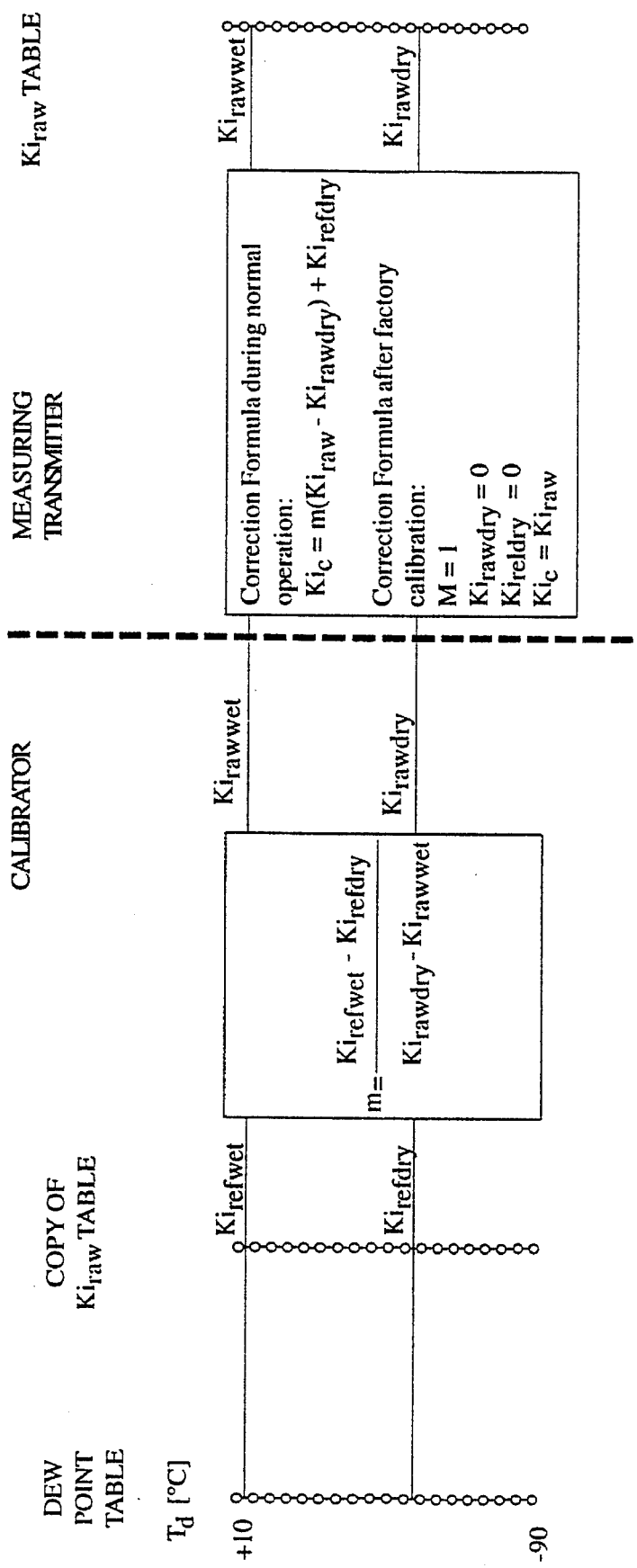
FIG. 12 is a function diagram of the moisture transmitter and the calibrator.

Once the slope is obtained, calibrator 34 transfers the values for m, $K_{rawdry}$, and $Ki_{refdry}$ and implements the values into the correction formula the measuring transmitter utilizes to put out corrected current counts $Ki_c$, thereby eliminating the drift the sensor has experienced. This is illustrated in FIG. 12 and in block 190 of FIG. 10. The correction formula used by measuring transmitter 10 is as follows:

$$Ki_c = m(Ki_{raw} - Ki_{rawdry}) + Ki_{refdry}$$

Calibrator 34 next verifies successful calibration as illustrated at block 192. A signal is sent to display 48 to provide an indication that the calibration procedure is complete as illustrated at block 194. The calibrator 34 is then removed from moisture transmitter 10 by reversing the mounting steps discussed above. This step is illustrated at block 196.

Therefore, the moisture transmitter 10 is recalibrated in the field without the need to move moisture transmitter 10 from process pipe 28. Recalibration takes place automatically without the need for the user to input any information into moisture transmitter 10.

It will be understood that while clock counts within a period of signals generated by the moisture sensor is a preferred variable used for recalibration, other variables that are a function of changes in dew point temperature may be used without departing from the scope and spirit of the present invention. Other variables may include the frequencies of the pulses corresponding to the capacitance of the sensor or the amperage the 4–20 mA signal generated as the output of the moisture transmitter. Thus, the present invention is not intended to be limited to the use of counts within a period as the variable used for recalibration.

Although the invention has been described in detail with reference to a certain preferred embodiment, variations and modifications exist within the scope and spirit of the present invention as described and defined in the following claims.

We claim:

1. An apparatus for calibrating a measuring transmitter which provides an output signal proportional to a parameter of interest measured by a sensor in the measuring transmitter without removing the measuring transmitter from its normal operating position, the apparatus comprising:

a housing;

a calibration sensor element located in the housing for sensing said parameter of interest;

a tube for coupling the housing to the measuring transmitter, thereby exposing the calibration sensor to the same parameter of interest as the measuring sensor in the measuring transmitter;

means for processing data related to the parameter of interest detected by the calibration sensor, for processing data related to the parameter of interest detected by the measuring sensor, for comparing the processed data related to the parameter of interest detected by the calibration sensor to processed data related to the parameter of interest detected by the measuring sensor, and for determining at least one correction value based on the comparison; and a communication link for transmitting data related to the parameter of interest detected by the measuring sensor to the data processing means and for transmitting the correction value to the measuring transmitter to recalibrate the measuring sensor.

2. The apparatus of claim 1, further comprising means for storing original calibration data related to the parameter of interest from the measuring transmitter, a maximum detected value of the parameter of interest from both the measuring sensor and the calibration sensor, and a minimum detected value of the parameter of interest for both the measuring sensor and the calibration sensor.

3. The apparatus of claim 2, further comprising a signal generator for generating a period having a variable length as a function of the parameter of interest being measured.

4. The apparatus of claim 3, further comprising a clock for generating equally spaced pulses.

5. The apparatus of claim 4, further comprising means for determining a count of pulses occurring within a period representing the maximum detected value of the parameter of interest for the calibration sensor, a period representing the maximum detected value of the parameter of interest from the measuring sensor, a period representing the minimum detected value of the parameter of interest for the calibration sensor, and a period representing the minimum detected value of the parameter of interest for the measuring sensor.

6. The apparatus of claim 5, wherein the processing means further calculates a difference between the original calibration data for the maximum detected value of the parameter of interest and the maximum detected value of the parameter of interest from the calibration sensor and a difference between the original calibration data for the minimum detected value of the parameter of interest and the minimum detected value of the parameter of interest from the calibration sensor.

7. The apparatus of claim 6, wherein the parameter of interest is dew point temperature.

8. The apparatus of claim 7, wherein the calibration sensor is an aluminum oxide sensor operating on a capacitance principle.

9. The apparatus of claim 1, further comprising a display unit coupled to the processing means to provide a visual indication of the progress of the calibrating means.

10. A method for recalibrating a measuring transmitter which provides an output signal proportional to a parameter of interest measured by a measuring sensor in the measuring transmitter without removing the measuring transmitter from its normal operating position, the method comprising the steps of:

providing a calibration sensor for sensing said parameter of interest;

connecting the calibration sensor to the measuring transmitter device, thereby exposing the calibration sensor to the same parameter of interest as the measuring sensor;

processing data related to the parameter of interest detected by the calibrating sensor;

comparing the processed data related to the parameter of interest detected by the calibrating sensor to processed data related to the parameter of interest detected by the measuring sensor; and providing a communication link between the calibration sensor and the measuring transmitter to recalibrate the measuring sensor automatically based on the comparing step.

11. The method of claim 10, further comprising the step of displaying information related to the recalibration to provide a visual indication of the progress of the recalibration.

* * * * *